(12) United States Patent
Wotton et al.

(10) Patent No.: US 9,393,367 B2
(45) Date of Patent: Jul. 19, 2016

(54) PREFILLED SYRINGES AND KITS THEREOF

(71) Applicant: Antares Pharma, Inc., Ewing, NJ (US)

(72) Inventors: Paul K. Wotton, Newtown, PA (US); Peter L. Sadowski, Woodbury, MN (US); Kaushik J. Dave, Ewing, NJ (US); Dominic P. Capone, Abington, PA (US)

(73) Assignee: ANTARES PHARMA, INC., Ewing, NJ (US)

( * ) Notice: Subject to any disclaimer, the term of this patent is extended or adjusted under 35 U.S.C. 154(b) by 0 days.

(21) Appl. No.: 14/678,449

(22) Filed: Apr. 3, 2015

(65) Prior Publication Data

US 2015/0209512 A1    Jul. 30, 2015

Related U.S. Application Data

(63) Continuation of application No. PCT/US2014/024530, filed on Mar. 12, 2014.

(60) Provisional application No. 61/778,398, filed on Mar. 12, 2013.

(51) Int. Cl.
*A61M 5/178* (2006.01)
*A61K 31/519* (2006.01)

(52) U.S. Cl.
CPC ............. *A61M 5/178* (2013.01); *A61K 31/519* (2013.01)

(58) Field of Classification Search
CPC ..................... A61M 5/178; A61M 2005/5026
See application file for complete search history.

(56) References Cited

U.S. PATENT DOCUMENTS

| | | |
|---|---|---|
| 3,688,765 A | 9/1972 | Gasaway |
| 3,712,301 A | 1/1973 | Sarnoff |
| 3,797,489 A | 3/1974 | Sarnoff |
| 3,882,863 A | 5/1975 | Sarnoff et al. |
| 4,484,910 A | 11/1984 | Sarnoff et al. |
| 4,558,690 A | 12/1985 | Joyce |
| 4,624,660 A | 11/1986 | Mijers et al. |
| 4,661,098 A | 4/1987 | Bekkering et al. |
| 4,664,653 A | 5/1987 | Sagstetter et al. |
| 4,678,461 A | 7/1987 | Mesa |
| 4,820,286 A | 4/1989 | van der Wal |
| 4,822,340 A | 4/1989 | Kamstra |
| 4,986,816 A | 1/1991 | Steiner et al. |
| 5,042,977 A | 8/1991 | Bechtold et al. |
| 5,078,680 A | 1/1992 | Sarnoff |
| 5,085,641 A | 2/1992 | Sarnoff et al. |
| 5,085,642 A | 2/1992 | Sarnoff et al. |
| 5,092,842 A | 3/1992 | Bechtold et al. |
| 5,102,393 A | 4/1992 | Sarnoff et al. |
| 5,114,406 A | 5/1992 | Gabriel et al. |
| 5,163,907 A | 11/1992 | Szuszkiewicz |
| 5,176,643 A | 1/1993 | Kramer et al. |
| 5,180,370 A | 1/1993 | Gillespie |
| 5,195,983 A | 3/1993 | Boese |
| 5,271,744 A | 12/1993 | Kramer et al. |
| 5,279,543 A | 1/1994 | Glikfeld et al. |
| 5,300,030 A | 4/1994 | Crossman et al. |
| 5,342,308 A | 8/1994 | Boschetti |
| 5,354,286 A | 10/1994 | Mesa et al. |
| 5,358,489 A | 10/1994 | Wyrick |
| 5,391,151 A | 2/1995 | Wilmot |
| 5,425,715 A | 6/1995 | Dalling et al. |
| 5,478,316 A | 12/1995 | Bitdinger et al. |
| 5,514,097 A | 5/1996 | Knauer |
| 5,540,664 A | 7/1996 | Wyrick |
| 5,567,160 A | 10/1996 | Massino |
| 5,569,192 A | 10/1996 | van der Wal |
| 5,593,388 A | 1/1997 | Phillips |
| 5,599,302 A | 2/1997 | Lilley et al. |
| 5,658,259 A | 8/1997 | Pearson et al. |
| 5,665,071 A | 9/1997 | Wyrick |
| 5,695,472 A | 12/1997 | Wyrick |
| 5,820,602 A | 10/1998 | Kovelman et al. |
| 5,836,911 A | 11/1998 | Marzynski et al. |
| 5,843,036 A | 12/1998 | Olive et al. |
| 5,851,197 A | 12/1998 | Marano et al. |
| 5,891,085 A | 4/1999 | Lilley et al. |
| 5,891,086 A | 4/1999 | Weston |
| 5,919,159 A | 7/1999 | Lilley et al. |
| 5,935,949 A | 8/1999 | White |
| 6,045,534 A | 4/2000 | Jacobson et al. |
| 6,077,247 A | 6/2000 | Marshall et al. |
| 6,090,070 A | 7/2000 | Hager et al. |
| 6,099,504 A | 8/2000 | Gross et al. |
| 6,203,529 B1 | 3/2001 | Gabriel et al. |
| 6,210,369 B1 | 4/2001 | Wilmot et al. |
| 6,221,046 B1 | 4/2001 | Burroughs et al. |
| 6,241,709 B1 | 6/2001 | Bechtold et al. |
| 6,270,479 B1 | 8/2001 | Bergens et al. |
| 6,371,939 B2 | 4/2002 | Bergens et al. |

(Continued)

FOREIGN PATENT DOCUMENTS

| | | |
|---|---|---|
| AR | 00081651 | 10/2012 |
| AU | 2008309660 | 4/2009 |
| AU | 2009299888 | 4/2010 |
| AU | 2010239762 | 12/2011 |
| AU | 2010242096 | 12/2011 |
| AU | 2010254627 | 1/2012 |
| AU | 2010260569 | 2/2012 |
| AU | 2010303987 | 5/2012 |
| AU | 2010332857 | 7/2012 |
| AU | 2010332862 | 7/2012 |
| AU | 2010337136 | 7/2012 |

(Continued)

*Primary Examiner* — Kevin C Sirmons
*Assistant Examiner* — Deanna K Hall
(74) *Attorney, Agent, or Firm* — Morgan, Lewis & Bockius LLP

(57) ABSTRACT

The present disclosure relates, in part, to a kit including at least two prefilled syringes. The first prefilled syringe includes a dose of a hazardous agent in a first volume of a pharmaceutical composition comprising a pharmaceutically acceptable solvent.

17 Claims, No Drawings

(56) References Cited

U.S. PATENT DOCUMENTS

| | | |
|---|---|---|
| 6,391,003 B1 | 5/2002 | Lesch, Jr. |
| 6,428,528 B2 | 8/2002 | Sadowski et al. |
| 6,517,517 B1 | 2/2003 | Farrugia et al. |
| 6,530,904 B1 | 3/2003 | Edwards et al. |
| 6,544,234 B1 | 4/2003 | Gabriel |
| 6,565,553 B2 | 5/2003 | Sadowski et al. |
| 6,569,123 B2 | 5/2003 | Alchas et al. |
| 6,569,143 B2 | 5/2003 | Alchas et al. |
| 6,607,508 B2 | 8/2003 | Knauer |
| 6,641,561 B1 | 11/2003 | Hill et al. |
| 6,656,150 B2 | 12/2003 | Hill et al. |
| 6,673,035 B1 | 1/2004 | Rice et al. |
| 6,682,504 B2 | 1/2004 | Nelson et al. |
| 6,746,429 B2 | 6/2004 | Sadowski et al. |
| 6,767,336 B1 | 7/2004 | Kaplan |
| 6,830,560 B1 | 12/2004 | Gross et al. |
| 6,932,793 B1 | 8/2005 | Marshall et al. |
| 6,932,794 B2 | 8/2005 | Giambattista et al. |
| 6,969,370 B2 | 11/2005 | Langley et al. |
| 6,969,372 B1 | 11/2005 | Halseth |
| 6,979,316 B1 | 12/2005 | Rubin et al. |
| 6,986,758 B2 | 1/2006 | Schiffmann |
| 6,997,901 B2 | 2/2006 | Popovsky |
| 7,066,907 B2 | 6/2006 | Crossman et al. |
| 7,118,553 B2 | 10/2006 | Scherer |
| 7,169,132 B2 | 1/2007 | Bendek et al. |
| 7,195,616 B2 | 3/2007 | Diller et al. |
| 7,218,962 B2 | 5/2007 | Freyman |
| 7,247,149 B2 | 7/2007 | Beyerlein |
| 7,291,132 B2 | 11/2007 | DeRuntz et al. |
| 7,292,885 B2 | 11/2007 | Scott et al. |
| 7,297,136 B2 | 11/2007 | Wyrick |
| 7,341,575 B2 | 3/2008 | Rice et al. |
| 7,361,160 B2 | 4/2008 | Hommann et al. |
| 7,390,314 B2 | 6/2008 | Stutz, Jr. et al. |
| 7,390,319 B2 | 6/2008 | Friedman |
| 7,407,492 B2 | 8/2008 | Gurtner |
| 7,416,540 B2 | 8/2008 | Edwards et al. |
| 7,449,012 B2 | 11/2008 | Young et al. |
| 7,488,308 B2 | 2/2009 | Lesch, Jr. |
| 7,488,313 B2 | 2/2009 | Segal et al. |
| 7,488,314 B2 | 2/2009 | Segal et al. |
| 7,517,342 B2 | 4/2009 | Scott et al. |
| 7,519,418 B2 | 4/2009 | Scott et al. |
| 7,544,188 B2 | 6/2009 | Edwards et al. |
| 7,547,293 B2 | 6/2009 | Williamson et al. |
| 7,569,035 B1 | 8/2009 | Wilmot et al. |
| 7,611,491 B2 | 11/2009 | Pickhard |
| 7,621,887 B2 | 11/2009 | Griffiths et al. |
| 7,621,891 B2 | 11/2009 | Wyrick |
| 7,635,348 B2 | 12/2009 | Raven et al. |
| 7,637,891 B2 | 12/2009 | Wall |
| 7,648,482 B2 | 1/2010 | Edwards et al. |
| 7,648,483 B2 | 1/2010 | Edwards et al. |
| 7,654,983 B2 | 2/2010 | De La Sema et al. |
| 7,658,724 B2 | 2/2010 | Rubin et al. |
| 7,670,314 B2 | 3/2010 | Wall et al. |
| 7,704,237 B2 | 4/2010 | Fisher et al. |
| 7,717,877 B2 | 5/2010 | Lavi et al. |
| 7,722,595 B2 | 5/2010 | Pettis et al. |
| 7,731,686 B2 | 6/2010 | Edwards et al. |
| 7,731,690 B2 | 6/2010 | Edwards et al. |
| 7,736,333 B2 | 6/2010 | Gillespie, III |
| 7,744,582 B2 | 6/2010 | Sadowski et al. |
| 7,749,194 B2 | 7/2010 | Edwards et al. |
| 7,749,195 B2 | 7/2010 | Hommann |
| 7,762,996 B2 | 7/2010 | Palasis |
| 7,776,015 B2 | 8/2010 | Sadowski et al. |
| 7,794,432 B2 | 9/2010 | Young et al. |
| 7,811,254 B2 | 10/2010 | Wilmot et al. |
| 7,862,543 B2 | 1/2011 | Potter et al. |
| 7,896,841 B2 | 3/2011 | Wall et al. |
| 7,901,377 B1 | 3/2011 | Harrison et al. |
| 7,905,352 B2 | 3/2011 | Wyrick |
| 7,905,866 B2 | 3/2011 | Haider et al. |
| 7,918,823 B2 | 4/2011 | Edwards et al. |
| 7,927,303 B2 | 4/2011 | Wyrick |
| 7,931,618 B2 | 4/2011 | Wyrick |
| 7,947,017 B2 | 5/2011 | Edwards et al. |
| RE42,463 E | 6/2011 | Landau |
| 7,955,304 B2 | 6/2011 | Guillermo |
| 7,967,772 B2 | 6/2011 | McKenzie et al. |
| 7,988,675 B2 | 8/2011 | Gillespie, III et al. |
| 8,016,774 B2 | 9/2011 | Freeman et al. |
| 8,016,788 B2 | 9/2011 | Edwards et al. |
| 8,021,335 B2 | 9/2011 | Lesch, Jr. |
| 8,048,035 B2 | 11/2011 | Mesa et al. |
| 8,048,037 B2 | 11/2011 | Kohlbrenner et al. |
| 8,057,427 B2 | 11/2011 | Griffiths et al. |
| 8,066,659 B2 | 11/2011 | Joshi et al. |
| 8,083,711 B2 | 12/2011 | Enggaard |
| 8,100,865 B2 | 1/2012 | Spofforth |
| 8,105,272 B2 | 1/2012 | Williamson et al. |
| 8,105,281 B2 | 1/2012 | Edwards et al. |
| 8,110,209 B2 | 2/2012 | Prestrelski et al. |
| 8,123,719 B2 | 2/2012 | Edwards et al. |
| 8,123,724 B2 | 2/2012 | Gillespie, III |
| 8,162,873 B2 | 4/2012 | Muto et al. |
| 8,162,886 B2 | 4/2012 | Sadowski et al. |
| 8,167,840 B2 | 5/2012 | Matusch |
| 8,167,866 B2 | 5/2012 | Klein |
| 8,177,758 B2 | 5/2012 | Brooks, Jr. et al. |
| 8,187,224 B2 | 5/2012 | Wyrick |
| 8,216,180 B2 | 7/2012 | Tschirren et al. |
| 8,216,192 B2 | 7/2012 | Burroughs et al. |
| 8,226,618 B2 | 7/2012 | Geertsen |
| 8,226,631 B2 | 7/2012 | Boyd et al. |
| 8,233,135 B2 | 7/2012 | Jansen et al. |
| 8,235,952 B2 | 8/2012 | Wikner |
| 8,246,577 B2 | 8/2012 | Schrul et al. |
| 8,251,947 B2 | 8/2012 | Kramer et al. |
| 8,257,318 B2 | 9/2012 | Thogersen et al. |
| 8,257,319 B2 | 9/2012 | Plumptre |
| 8,267,899 B2 | 9/2012 | Moller |
| 8,267,900 B2 | 9/2012 | Harms et al. |
| 8,273,798 B2 | 9/2012 | Bausch et al. |
| 8,275,454 B2 | 9/2012 | Adachi et al. |
| 8,276,583 B2 | 10/2012 | Farieta et al. |
| 8,277,412 B2 | 10/2012 | Kronestedt |
| 8,277,413 B2 | 10/2012 | Kirchhofer |
| 8,298,175 B2 | 10/2012 | Hirschel et al. |
| 8,298,194 B2 | 10/2012 | Moller |
| 8,300,852 B2 | 10/2012 | Terada |
| RE43,834 E | 11/2012 | Steenfeldt-Jensen et al. |
| 8,308,232 B2 | 11/2012 | Zamperla et al. |
| 8,308,695 B2 | 11/2012 | Laiosa |
| 8,313,466 B2 | 11/2012 | Edwards et al. |
| 8,317,757 B2 | 11/2012 | Plumptre |
| 8,323,237 B2 | 12/2012 | Radmer et al. |
| 8,333,739 B2 | 12/2012 | Moller |
| 8,337,472 B2 | 12/2012 | Edginton et al. |
| 8,343,103 B2 | 1/2013 | Moser |
| 8,343,109 B2 | 1/2013 | Marshall et al. |
| 8,348,905 B2 | 1/2013 | Radmer et al. |
| 8,353,878 B2 | 1/2013 | Moller et al. |
| 8,357,120 B2 | 1/2013 | Moller et al. |
| 8,357,125 B2 | 1/2013 | Grunhut et al. |
| 8,361,036 B2 | 1/2013 | Moller et al. |
| 8,366,680 B2 | 2/2013 | Raab |
| 8,372,031 B2 | 2/2013 | Elmen et al. |
| 8,372,042 B2 | 2/2013 | Wieselblad |
| 8,376,993 B2 | 2/2013 | Cox et al. |
| 8,398,593 B2 | 3/2013 | Eich et al. |
| 8,409,149 B2 | 4/2013 | Hommann et al. |
| 8,435,215 B2 | 5/2013 | Abry et al. |
| 8,664,231 B2* | 3/2014 | Will ............... A61K 9/0019 514/262.1 |
| 2001/0039394 A1 | 11/2001 | Weston |
| 2002/0173752 A1 | 11/2002 | Polzin |
| 2003/0040697 A1 | 2/2003 | Pass et al. |
| 2003/0171717 A1 | 9/2003 | Farrugia et al. |
| 2004/0039337 A1 | 2/2004 | Letzing |
| 2004/0176381 A1* | 9/2004 | Walsh ............... A61J 1/035 514/251 |

(56) References Cited

U.S. PATENT DOCUMENTS

| | | |
|---|---|---|
| 2004/0267355 A1 | 12/2004 | Scott et al. |
| 2005/0027255 A1 | 2/2005 | Lavi et al. |
| 2005/0101919 A1 | 5/2005 | Brunnberg |
| 2005/0165363 A1 | 7/2005 | Judson et al. |
| 2005/0209569 A1 | 9/2005 | Ishikawa et al. |
| 2005/0215955 A1 | 9/2005 | Slawson |
| 2005/0240145 A1 | 10/2005 | Scott et al. |
| 2005/0256499 A1 | 11/2005 | Pettis et al. |
| 2005/0273054 A1 | 12/2005 | Asch |
| 2006/0106362 A1 | 5/2006 | Pass et al. |
| 2006/0129122 A1 | 6/2006 | Wyrick |
| 2006/0224124 A1 | 10/2006 | Scherer |
| 2006/0258988 A1 | 11/2006 | Keitel et al. |
| 2007/0017533 A1 | 1/2007 | Wyrick |
| 2007/0025890 A1 | 2/2007 | Joshi et al. |
| 2007/0027430 A1 | 2/2007 | Hommann |
| 2007/0100288 A1 | 5/2007 | Bozeman et al. |
| 2007/0123818 A1 | 5/2007 | Griffiths et al. |
| 2007/0129687 A1 | 6/2007 | Marshall et al. |
| 2007/0185432 A1 | 8/2007 | Etheredge et al. |
| 2007/0191784 A1 | 8/2007 | Jacobs et al. |
| 2007/0219498 A1 | 9/2007 | Malone et al. |
| 2008/0059133 A1 | 3/2008 | Edwards et al. |
| 2008/0154199 A1 | 6/2008 | Wyrick |
| 2008/0262427 A1 | 10/2008 | Hommann |
| 2008/0262436 A1 | 10/2008 | Olson |
| 2008/0262445 A1 | 10/2008 | Hsu et al. |
| 2009/0124981 A1 | 5/2009 | Evans |
| 2009/0124997 A1 | 5/2009 | Pettis et al. |
| 2009/0204062 A1 | 8/2009 | Muto et al. |
| 2009/0299278 A1 | 12/2009 | Lesch, Jr. et al. |
| 2009/0304812 A1 | 12/2009 | Staniforth et al. |
| 2009/0318361 A1 | 12/2009 | Noera et al. |
| 2010/0036318 A1 | 2/2010 | Raday et al. |
| 2010/0049125 A1 | 2/2010 | James et al. |
| 2010/0069845 A1 | 3/2010 | Marshall et al. |
| 2010/0076378 A1 | 3/2010 | Runfola |
| 2010/0076400 A1 | 3/2010 | Wall |
| 2010/0087847 A1 | 4/2010 | Hong |
| 2010/0094214 A1 | 4/2010 | Abry et al. |
| 2010/0094324 A1 | 4/2010 | Huang et al. |
| 2010/0100039 A1 | 4/2010 | Wyrick |
| 2010/0152699 A1 | 6/2010 | Ferrari et al. |
| 2010/0152702 A1 | 6/2010 | Vigil et al. |
| 2010/0160894 A1 | 6/2010 | Julian et al. |
| 2010/0168677 A1 | 7/2010 | Gabriel et al. |
| 2010/0174268 A1 | 7/2010 | Wilmot et al. |
| 2010/0204678 A1 | 8/2010 | Imran |
| 2010/0217105 A1 | 8/2010 | Yodfat et al. |
| 2010/0228193 A1 | 9/2010 | Wyrick |
| 2010/0249746 A1 | 9/2010 | Klein |
| 2010/0256570 A1 | 10/2010 | Maritan |
| 2010/0262082 A1 | 10/2010 | Brooks et al. |
| 2010/0274198 A1 | 10/2010 | Bechtold |
| 2010/0274273 A1 | 10/2010 | Schraga et al. |
| 2010/0288593 A1 | 11/2010 | Chiesa et al. |
| 2010/0292643 A1 | 11/2010 | Wilmot et al. |
| 2010/0298780 A1 | 11/2010 | Laiosa |
| 2010/0312196 A1 | 12/2010 | Hirschel et al. |
| 2010/0318035 A1 | 12/2010 | Edwards et al. |
| 2010/0318037 A1 | 12/2010 | Young et al. |
| 2010/0324480 A1 | 12/2010 | Chun |
| 2011/0021989 A1 | 1/2011 | Janek et al. |
| 2011/0054414 A1 | 3/2011 | Shang et al. |
| 2011/0077599 A1 | 3/2011 | Wozencroft |
| 2011/0087192 A1 | 4/2011 | Uhland et al. |
| 2011/0098655 A1 | 4/2011 | Jennings et al. |
| 2011/0125076 A1 | 5/2011 | Kraft et al. |
| 2011/0125100 A1 | 5/2011 | Schwirtz et al. |
| 2011/0137246 A1 | 6/2011 | Cali et al. |
| 2011/0144594 A1 | 6/2011 | Sund et al. |
| 2011/0190725 A1 | 8/2011 | Pettis et al. |
| 2011/0196300 A1 | 8/2011 | Edwards et al. |
| 2011/0196311 A1 | 8/2011 | Bicknell et al. |
| 2011/0224620 A1 | 9/2011 | Johansen et al. |
| 2011/0238003 A1 | 9/2011 | Bruno-Raimondi et al. |
| 2011/0269750 A1 | 11/2011 | Kley et al. |
| 2011/0319864 A1 | 12/2011 | Beller et al. |
| 2012/0004608 A1 | 1/2012 | Lesch, Jr. |
| 2012/0016296 A1 | 1/2012 | Charles |
| 2012/0046609 A1 | 2/2012 | Mesa et al. |
| 2012/0053563 A1 | 3/2012 | Du |
| 2012/0059319 A1 | 3/2012 | Segal |
| 2012/0071829 A1 | 3/2012 | Edwards et al. |
| 2012/0095443 A1 | 4/2012 | Ferrari et al. |
| 2012/0101475 A1 | 4/2012 | Wilmot et al. |
| 2012/0116318 A1 | 5/2012 | Edwards et al. |
| 2012/0123350 A1 | 5/2012 | Giambattista et al. |
| 2012/0123385 A1 | 5/2012 | Edwards et al. |
| 2012/0130318 A1 | 5/2012 | Young |
| 2012/0130342 A1 | 5/2012 | Cleathero |
| 2012/0136303 A1 | 5/2012 | Cleathero |
| 2012/0136318 A1 | 5/2012 | Lanin et al. |
| 2012/0143144 A1 | 6/2012 | Young |
| 2012/0157931 A1 | 6/2012 | Nzike |
| 2012/0157965 A1 | 6/2012 | Wotton et al. |
| 2012/0172809 A1 | 7/2012 | Plumptre |
| 2012/0172811 A1 | 7/2012 | Enggaard et al. |
| 2012/0172812 A1 | 7/2012 | Plumptre et al. |
| 2012/0172813 A1 | 7/2012 | Plumptre et al. |
| 2012/0172814 A1 | 7/2012 | Plumptre et al. |
| 2012/0172815 A1 | 7/2012 | Holmqvist |
| 2012/0172816 A1 | 7/2012 | Boyd et al. |
| 2012/0172818 A1 | 7/2012 | Harms et al. |
| 2012/0179100 A1 | 7/2012 | Sadowski et al. |
| 2012/0179137 A1 | 7/2012 | Bartlett et al. |
| 2012/0184900 A1 | 7/2012 | Marshall et al. |
| 2012/0184917 A1 | 7/2012 | Bom et al. |
| 2012/0184918 A1 | 7/2012 | Bostrom |
| 2012/0186075 A1 | 7/2012 | Edginton |
| 2012/0191048 A1 | 7/2012 | Eaton |
| 2012/0191049 A1 | 7/2012 | Harms et al. |
| 2012/0197209 A1 | 8/2012 | Bicknell et al. |
| 2012/0197213 A1 | 8/2012 | Kohlbrenner et al. |
| 2012/0203184 A1 | 8/2012 | Selz et al. |
| 2012/0203185 A1 | 8/2012 | Kristensen et al. |
| 2012/0203186 A1 | 8/2012 | Vogt et al. |
| 2012/0209192 A1 | 8/2012 | Alexandersson |
| 2012/0209200 A1 | 8/2012 | Jones et al. |
| 2012/0209210 A1 | 8/2012 | Plumptre et al. |
| 2012/0209211 A1 | 8/2012 | Plumptre et al. |
| 2012/0209212 A1 | 8/2012 | Plumptre et al. |
| 2012/0215162 A1 | 8/2012 | Nielsen et al. |
| 2012/0215176 A1 | 8/2012 | Veasey et al. |
| 2012/0220929 A1 | 8/2012 | Nagel et al. |
| 2012/0220941 A1 | 8/2012 | Jones |
| 2012/0220953 A1 | 8/2012 | Holmqvist |
| 2012/0220954 A1 | 8/2012 | Cowe |
| 2012/0226226 A1 | 9/2012 | Edwards et al. |
| 2012/0230620 A1 | 9/2012 | Holdgate et al. |
| 2012/0232517 A1 | 9/2012 | Saiki |
| 2012/0245516 A1 | 9/2012 | Tschirren et al. |
| 2012/0245532 A1 | 9/2012 | Frantz et al. |
| 2012/0253274 A1 | 10/2012 | Karlsson et al. |
| 2012/0253287 A1 | 10/2012 | Giambattista et al. |
| 2012/0253288 A1 | 10/2012 | Dasbach et al. |
| 2012/0253289 A1 | 10/2012 | Cleathero |
| 2012/0253290 A1 | 10/2012 | Geertsen |
| 2012/0253314 A1 | 10/2012 | Harish et al. |
| 2012/0259285 A1 | 10/2012 | Schabbach et al. |
| 2012/0265153 A1 | 10/2012 | Jugl et al. |
| 2012/0267761 A1 | 10/2012 | Kim et al. |
| 2012/0271233 A1 | 10/2012 | Bruggemann et al. |
| 2012/0271243 A1 | 10/2012 | Plumptre et al. |
| 2012/0277724 A1 | 11/2012 | Larsen et al. |
| 2012/0283645 A1 | 11/2012 | Veasey et al. |
| 2012/0283648 A1 | 11/2012 | Veasey et al. |
| 2012/0283649 A1 | 11/2012 | Veasey et al. |
| 2012/0283650 A1 | 11/2012 | MacDonald et al. |
| 2012/0283651 A1 | 11/2012 | Veasey et al. |
| 2012/0283652 A1 | 11/2012 | MacDonald et al. |
| 2012/0283654 A1 | 11/2012 | MacDonald et al. |
| 2012/0283660 A1 | 11/2012 | Jones et al. |
| 2012/0283661 A1 | 11/2012 | Jugl et al. |

(56) References Cited

U.S. PATENT DOCUMENTS

| | | | |
|---|---|---|---|
| 2012/0289907 A1 | 11/2012 | Veasey et al. |
| 2012/0289908 A1 | 11/2012 | Kouyoumjian et al. |
| 2012/0289909 A1 | 11/2012 | Raab et al. |
| 2012/0289929 A1 | 11/2012 | Boyd et al. |
| 2012/0291778 A1 | 11/2012 | Nagel et al. |
| 2012/0296276 A1 | 11/2012 | Nicholls et al. |
| 2012/0296287 A1 | 11/2012 | Veasey et al. |
| 2012/0302989 A1 | 11/2012 | Kramer et al. |
| 2012/0302992 A1 | 11/2012 | Brooks et al. |
| 2012/0310156 A1 | 12/2012 | Karlsson et al. |
| 2012/0310206 A1 | 12/2012 | Kouyoumjian et al. |
| 2012/0310208 A1 | 12/2012 | Kirchhofer |
| 2012/0310289 A1 | 12/2012 | Bottlang et al. |
| 2012/0316508 A1 | 12/2012 | Kirchhofer |
| 2012/0323177 A1 | 12/2012 | Adams et al. |
| 2012/0323186 A1 | 12/2012 | Karlsen et al. |
| 2012/0325865 A1 | 12/2012 | Forstreuter et al. |
| 2012/0330228 A1 | 12/2012 | Day et al. |
| 2013/0006191 A1 | 1/2013 | Jugl et al. |
| 2013/0006192 A1 | 1/2013 | Teucher et al. |
| 2013/0006193 A1 | 1/2013 | Veasey et al. |
| 2013/0006310 A1 | 1/2013 | Bottlang et al. |
| 2013/0012871 A1 | 1/2013 | Pommereu |
| 2013/0012884 A1 | 1/2013 | Pommerau et al. |
| 2013/0012885 A1 | 1/2013 | Bode et al. |
| 2013/0018310 A1 | 1/2013 | Boyd et al. |
| 2013/0018313 A1 | 1/2013 | Kramer et al. |
| 2013/0018317 A1 | 1/2013 | Bobroff et al. |
| 2013/0018323 A1 | 1/2013 | Boyd et al. |
| 2013/0018327 A1 | 1/2013 | Dasbach et al. |
| 2013/0018328 A1 | 1/2013 | Jugl et al. |
| 2013/0023830 A1 | 1/2013 | Bode |
| 2013/0030367 A1 | 1/2013 | Wotton et al. |
| 2013/0030378 A1 | 1/2013 | Jugl et al. |
| 2013/0030383 A1 | 1/2013 | Keitel |
| 2013/0030409 A1 | 1/2013 | Macdonald et al. |
| 2013/0035641 A1 | 2/2013 | Moller et al. |
| 2013/0035642 A1 | 2/2013 | Daniel |
| 2013/0035644 A1 | 2/2013 | Giambattista et al. |
| 2013/0035645 A1 | 2/2013 | Bicknell et al. |
| 2013/0035647 A1 | 2/2013 | Veasey et al. |
| 2013/0041321 A1 | 2/2013 | Cross et al. |
| 2013/0041324 A1 | 2/2013 | Daniel |
| 2013/0041325 A1 | 2/2013 | Helmer et al. |
| 2013/0041327 A1 | 2/2013 | Daniel |
| 2013/0041328 A1 | 2/2013 | Daniel |
| 2013/0041347 A1 | 2/2013 | Daniel |
| 2013/0060231 A1 | 3/2013 | Adlon et al. |

FOREIGN PATENT DOCUMENTS

| | | |
|---|---|---|
| AU | 2010338469 | 7/2012 |
| AU | 2011214922 | 8/2012 |
| AU | 2011221472 | 8/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| BR | 0208013 | 3/2004 |
| BR | PI712805 | 10/2012 |
| BR | PI0713802-4 | 11/2012 |
| CA | 2552177 | 7/1999 |
| CA | 02702412 | 12/2008 |
| CN | 101128231 | 2/2008 |
| CN | 101400394 | 4/2009 |
| CN | 101479000 | 7/2009 |
| CN | 101516421 | 8/2009 |
| CN | 101563124 | 10/2009 |
| CN | 101678172 | 3/2010 |
| CN | 101687078 | 3/2010 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 102630172 | 8/2012 |
| CN | 102630173 | 8/2012 |
| CN | 102630174 | 8/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| DE | 102006041809 | 3/2008 |
| DK | 2229201 | 7/2012 |
| DK | 2274032 | 10/2012 |
| DK | 02346552 | 11/2012 |
| EP | 245895 | 11/1987 |
| EP | 361668 | 4/1990 |
| EP | 525525 | 2/1993 |
| EP | 1307012 | 5/2003 |
| EP | 1140260 | 8/2005 |
| EP | 2174682 | 4/2010 |
| EP | 2364742 | 9/2011 |
| EP | 2471564 | 7/2012 |
| EP | 02477681 | 7/2012 |
| EP | 02484395 | 8/2012 |
| EP | 2526987 | 11/2012 |
| ES | 02385630 | 7/2012 |
| ES | 2389866 | 11/2012 |
| GB | 2463034 | 3/2010 |
| IL | 171247 | 8/2012 |
| IL | 198750 | 10/2012 |
| JP | 5016490 | 5/2008 |
| JP | 5026411 | 11/2008 |
| JP | 5033792 | 11/2008 |
| JP | 2009-529395 | 8/2009 |
| JP | 5039135 | 11/2009 |
| JP | 5044625 | 12/2009 |
| JP | 2010-005414 | 1/2010 |
| JP | 2010-046507 | 3/2010 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012-525185 | 10/2012 |
| JP | 2012523876 | 10/2012 |
| JP | 2012525200 | 10/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| NO | 332622 | 10/2003 |
| NZ | 00590352 | 10/2012 |

(56) References Cited

FOREIGN PATENT DOCUMENTS

| | | |
|---|---|---|
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| WO | WO 88/08724 | 11/1988 |
| WO | WO 91/13299 | 9/1991 |
| WO | WO 91/13430 | 9/1991 |
| WO | WO 94/11041 | 5/1994 |
| WO | WO 9831369 | 7/1998 |
| WO | WO 9832451 | 7/1998 |
| WO | WO 9922789 | 5/1999 |
| WO | WO 9962525 | 12/1999 |
| WO | WO 0006228 | 2/2000 |
| WO | WO 02/083216 | 10/2002 |
| WO | WO 02089805 | 11/2002 |
| WO | WO 03047663 | 6/2003 |
| WO | WO 03068290 | 8/2003 |
| WO | WO 03070296 | 8/2003 |
| WO | WO 03097133 | 11/2003 |
| WO | WO 2004/041331 | 5/2004 |
| WO | WO 2004/047892 | 6/2004 |
| WO | WO 2005/005929 | 1/2005 |
| WO | WO 2005/009515 | 2/2005 |
| WO | WO 2005/053778 | 6/2005 |
| WO | WO 2006/079064 | 7/2006 |
| WO | WO 2006/130098 | 12/2006 |
| WO | WO 2007/100899 | 9/2007 |
| WO | WO 2007/104636 | 9/2007 |
| WO | WO 2007/129106 | 11/2007 |
| WO | WO 2007/131013 | 11/2007 |
| WO | WO 2007/131025 | 11/2007 |
| WO | WO 2007/143676 | 12/2007 |
| WO | WO 2008/005315 | 1/2008 |
| WO | WO 2008/009476 | 1/2008 |
| WO | WO 2008/071804 | 6/2008 |
| WO | WO 2008/100576 | 8/2008 |
| WO | WO 2009049885 | 4/2009 |
| WO | WO 2009/114542 | 9/2009 |
| WO | WO 2009/132778 | 11/2009 |
| WO | WO 2010/003569 | 1/2010 |
| WO | WO 2010/043533 | 4/2010 |
| WO | WO 2010/097116 | 9/2010 |
| WO | WO 2010/108116 | 9/2010 |
| WO | WO 2011/023736 | 3/2011 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/042537 | 4/2011 |
| WO | WO 2011/042540 | 4/2011 |
| WO | WO 2011/043714 | 4/2011 |
| WO | WO 2011/067615 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/101375 | 8/2011 |
| WO | WO 2011/111006 | 9/2011 |
| WO | WO 2012020084 | 2/2012 |
| WO | WO 2012022771 | 2/2012 |
| WO | WO 2012/090186 | 7/2012 |
| WO | WO 2012/122643 | 9/2012 |

* cited by examiner

PREFILLED SYRINGES AND KITS THEREOF

CROSS REFERENCE TO RELATED APPLICATIONS

The present application is a continuation of International Application No. PCT/US2014/024530 filed Mar. 12, 2014, which claims priority to U.S. Provisional Patent Application No. 61/778,398 filed Mar. 12, 2013, each of which incorporated by reference in its entirety herein for all purposes.

BACKGROUND OF THE INVENTION

Since the late 1980's hazardous agents, such as cytotoxic agents, have been useful in managing and treating a number of diseases such as rheumatoid arthritis (and other autoimmune diseases), juvenile rheumatoid arthritis, psoriasis, psoriatic arthritis, systemic lupus erythematosus, steroid-resistant polymyositis or dermatomyositis, Wegener's granulomatosis, polyarteritis nodosa, hormonal imbalances, and some forms of vasculitis. Hazardous agents tend to exhibit side effects, however, that are harmful or toxic to the subject. Many of these side effects occur when hazardous agents are administered orally, but the oral form is generally the preferred method of delivery of these agents due to its ease of use.

In addition to increased toxicity, variable and reduced bioavailability has been observed for some hazardous agents, such as methotrexate, that are orally administered. These limitations are particularly demonstrated when the oral dosing is escalated beyond 15 mg per week. It has been suggested that with parenteral administration, such as by injection, more predictable, reproducible and complete bioavailability along with better therapeutic results could be achieved, particularly at higher dosages.

Only about 7% of the prescriptions for methotrexate written by rheumatologists are for an injectable formulation. Reasons for prescribing methotrexate injections are usually to improve bioavailability or to alleviate side effects. Physicians have expressed interest in increasing the number of prescriptions for cytotoxic agent injections, and particularly injections for home use and administration by a patient. This is generally not considered feasible because it is not possible to ensure that patients can reliably and repeatably draw an accurate dose from vials and correctly administer the product by subcutaneous (SC) injection, especially with agents used to treat patients suffering from certain debilitating diseases. Additionally, the toxicity of hazardous agents increases the risk that non-users of the injections will come into contact with the cytotoxic agents in a home setting. Insufficient data exists on the effect of low dose, chronic exposure to hazardous agents that are, or may be, candidates for home use or self-injection. In the absence of such information, practice guidelines direct one to assume a high degree risk for injectable hazardous agents such as methotrexate, with the recommendation of formal directives and risk assessments, including formal training and mitigation strategies, to minimize risk (see Oliver, S., and Livermore, P., Administering subcutaneous methotrexate for inflammatory arthritis: RCN guidance for nurses, 2004; Royal College of Nursing, Wyeth, Publication Code 002 269). Specific directives include: preparation of syringes in dedicated pharmacies with aseptic preparation areas; administration performed in specific locations and only by adequately trained personnel; spillage kits located proximal to use areas; accounting for all who may be at risk in the event of an accident; and audits to assess compliance and execution of risk mitigation strategies. Because of the need for such directives, and thus the large number of precautions that must be learned and followed in order to safely inject a hazardous agent, it is presently thought that it is not practical for hazardous agents, and particularly methotrexate, to be self-injected by a patient outside of a clinical setting or without the assistance of a health care provider.

BRIEF SUMMARY OF THE INVENTION

In one aspect, the present invention provides a kit including at least one first prefilled syringe, the first prefilled syringe includes a dose of a hazardous agent in a first volume of a pharmaceutical composition comprising a pharmaceutically acceptable solvent, wherein the dose of the hazardous agent is in a range of from about 7.5 mg to about 25 mg

DETAILED DESCRIPTION OF THE INVENTION

A. Prefilled Syringes

In one aspect, the present invention provides a kit including at least one first prefilled syringe and instruction for use. In one embodiment, the instruction for use includes a prescription drug information. In some embodiments, the instruction for use includes one or more information items selected from the group consisting of a physician name, a physician telephone number, a pharmacy name, a pharmacy address, a pharmacy telephone number, a medication name, a medication dosage, a frequency at which the medication is to be taken, a manner in which the medication is to be taken, an ailment for which the medication is being prescribed, a physical description of the medication, a marking on the medication, a preferred range of dosages, the size of each unit of medication, a weight of each unit of medication, a special warning, a special instruction, an expiration date of the medication, a proper storage condition for the medication, a possible side effect of the medication, a recommendation to avoid a side effect of the medication, drug interaction information, a Food and Drug Administration (FDA) update, an FDA warning, recall information, Physician's Desk Reference (PDR) information on the medication, a PDR update on the medication, and existence of a generic form of the medication.

In one embodiment, the first prefilled syringe includes a dose of an agent (e.g., a hazardous agent) in a first volume of a pharmaceutical composition. In one embodiment, the pharmaceutical composition includes a pharmaceutically acceptable solvent. In such an embodiment, the first volume of the pharmaceutical composition in the first prefilled syringe is substantially the same as a second volume of the pharmaceutical composition in a second prefilled syringe containing the same hazardous agent. In one embodiment, "substantially the same" means the volumes are within 0.1 ml of each other. In one embodiment, "substantially the same" means the volumes are within 10% of each other. In one embodiment, "substantially the same" means the volumes are within 15% of each other.

Maintaining the same volume of the pharmaceutical composition across different concentrations of the same hazardous agent is important in treatment in general, but is particularly important in hazardous agent dose titration, because, inter alia, the patient habituates to the injected volume of the hazardous agent. Habituating to the injected volume of the hazardous agent, reduces the patient's likelihood of experiencing injection site reactions and/or other conditioned responses following subsequent injections of the hazardous agent at the same volume.

In one embodiment, the second prefilled syringe is included in the first kit and thusly the first kit includes two or more pre-filled syringes. In one embodiment, the second prefilled syringe is included in a second kit, wherein the second kit includes at least one prefilled syringe, the at least one prefilled syringe including the same hazardous agent in the second volume of the pharmaceutical composition, and thusly the first kit includes one or more pre-filled syringes.

Similarly, in some embodiments, two or more medical kits are provided. In one embodiment, the first kit includes at least one first prefilled syringe, the first prefilled syringe including a dose of a hazardous agent in a first volume of a pharmaceutical composition comprising a pharmaceutically acceptable solvent; the second kit including at least one second prefilled syringe, the second prefilled syringe including a dose of the hazardous agent in a second volume of a pharmaceutical composition comprising a pharmaceutically acceptable solvent, wherein the first volume of the pharmaceutical composition and the second volume of the pharmaceutical agent are substantially the same. In one embodiment, each of two or more kits include a dose of the hazardous agent in a range of from about 7.5 mg to about 25 mg. In another embodiment, each prefilled syringe includes 50 mg, 75 mg or 100 mg of the medicament.

In one embodiment, the hazardous agent is present in the pharmaceutical composition in a concentration ranging from about 18.5 mg/ml to about 62.5 mg/ml. In one embodiment, the dose of the hazardous agent is selected from the group consisting of about 7.5 mg, about 10 mg, about 12.5 mg, about 15 mg, about 17.5 mg, about 20 mg, about 22.5 mg, and about 25 mg. In one embodiment, the volume of the pharmaceutical composition is selected from the group consisting of about 0.1 ml, about 0.2 ml, about 0.3 ml, about 0.32 ml, and about 0.4 ml. In certain embodiments, the volume of fluid contained in the prefilled syringe can be about 0.3 to 0.4 ml, 0.32 to 0.4 ml, about 0.1 to 0.5 ml or greater than 0.01 ml but less than or equal to 1 ml.

In one embodiment, the dose of the hazardous agent comprises methotrexate. In another embodiment, the hazardous agent comprises testosterone. In one embodiment, each prefilled syringe is configured for subcutaneous administration of the hazardous agent.

In one exemplary embodiment, the kit of the present invention comprises a pharmaceutical composition having a pharmaceutically acceptable solvent. In one embodiment, the pharmaceutically acceptable solvent comprises water. In one embodiment, the pharmaceutically acceptable solvent comprises ethanol. In one embodiment, the pharmaceutically acceptable solvent comprises water and ethanol. In one embodiment, the volume of the pharmaceutical composition ranges from about 0.1 ml to about 0.5 ml. In one embodiment, the volume of the pharmaceutical composition is about 0.5 ml. In one embodiment, the volume of the pharmaceutical composition is about 0.4 ml. In one embodiment, the volume of the pharmaceutical composition is about 0.3 ml. In one embodiment, the volume of the pharmaceutical composition is about 0.32 ml.

In one exemplary embodiment, the kit of the present invention comprises the hazardous agent in a dose of about 7.5 mg. In one embodiment, the dose of the hazardous agent is about 10 mg. In one embodiment, the dose of the hazardous agent is about 12.5 mg. In one embodiment, wherein the dose of the hazardous agent is about 15 mg. In one embodiment, the dose of the hazardous agent is about 17.5 mg. In one embodiment, the dose of the hazardous agent is about 20 mg. In one embodiment, the dose of the hazardous agent is about 22.5 mg. In one embodiment, the dose of the hazardous agent is about 25 mg. In one embodiment, the dose of the hazardous agent is selected from the group consisting of 7.5 mg, about 10 mg, about 12.5 mg, about 15 mg, about 17.5 mg, about 20 mg, about 22.5 mg, and about 25 mg and the volume of the pharmaceutical composition is selected from the group consisting of about 0.3 ml, about 0.32 ml, and about 0.4 ml.

In some exemplary embodiments of the kit of the present invention, each prefilled syringe is configured for use with an automatic injector (e.g., an autoinjector). In one embodiment, the autoinjector in combination with each prefilled syringe are designed to allow a user to self-administer a pre-measured subcutaneous dose of the hazardous agent. Examples of autoinjector devices suitable for use with the kits and methods of treatment in accordance with the present invention include, but are not limited to, those disclosed in U.S. Patent Application Publication No. 2012/0157965 entitled "Hazardous Agent Injection System" (to Paul Wotton et. al, published Jun. 21, 2012), which is incorporated by reference herein in its entirety. Subcutaneous administration of the hazardous agent with these autoinjectors may be carried out in accordance with the methods disclosed in the U.S. Patent Application Publication No. 2012/0157965, or instructions typically supplied with the autoinjectors.

In some embodiments, the present invention provides at least one kit configured for hazardous agent dose titration, wherein the at least one kit includes one or more prefilled syringes, the one or more prefilled syringes including substantially the same volume of a pharmaceutical composition, wherein the pharmaceutical composition includes the same hazardous agent. In one embodiment, the one or more prefilled syringes include substantially the same volume of the pharmaceutical composition but different concentration of the hazardous agent. In one embodiment, the kit of the present invention includes 1, 2, 3, 4, 5, or more prefilled syringes.

B. Agents for Use

Agents which may be used with the kits and methods of the present invention include those listed in the Physicians' Desk Reference (PDR®), 67th Edition (2013), and include, without limitation, allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antibiotics, antiviral antibiotics, anticancer preparations, anticholinergic drug inhibitors, anticoagulants, anticonvulsants, antidepressants, antidiabetic agents, antidiarrheals, antidiuretics, antienuresis agents, antifibrinolytic agents, antifibrotics (systemic), antiflatulents, antifungal agents, antigonadotropin, antihistamines, antihyperammonia agents, anti-inflammatory agents, antimalarials, antimetabolites, antimigraine preparations, antinauseants, antineoplastics, anti-obesity preparations, antiparasitics, anti-parkinsonism drugs, antipruritics, antipyretics, antispasmodics and antichloinergics, antitoxoplasmosis agents, antitussives, antivertigo agents, antiviral agents, biologicals, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, cough and cold preparations, decongestants, expectorants and combinations, diuretics, emetics, enzymes and digestants, fertility agents, fluorine preparations, galactokinetic agents, geriatrics, germicides, hematinics, hemorrhoidal preparations, histamine H. receptor antagonists, hormones, hydrocholeretics, hyperglycemic agents, hypnotics, immunosuppressives, laxatives, mucolytics, muscle relaxants, narcotic antagonists, narcotic detoxification agents, ophthalmological osmotic dehydrating agents, otic preparations, oxytocics, parashypatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics, thrombolytics, thyroid preparations, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the PDR®.

In some embodiments, suitable agent for use can be any medicament. In other embodiments, the agent may be a hazardous agent. "Hazardous Agent(s)" as used herein means any one or more medications that are toxic agents, cytotoxic agents and/or other dangerous agents that may cause serious effects upon contact with a subject as well as highly potent agents, agents that have profound physiological effects at low doses. Exemplary hazardous agents include, without limitation, analgesics, anti-retroviral medicaments, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. Examples of hazardous agents suitable for use with the kits and methods of treatment in accordance with the present invention include, but are not limited to, those disclosed in U.S. Patent Application Publication No. 2012/0157965 entitled "Hazardous Agent Injection System" (to Paul Wotton et. al, published Jun. 21, 2012), which is incorporated by reference herein in its entirety. Particular examples of cytotoxic agents include, without limitation, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, and derivatives thereof. Examples of highly potent agents include, without limitation, steroids such as dexamethasone, progesterone, somatostatin, and analogues thereof; biologically active peptides such as glucagon-like peptide-1 agonists including exenatide, parathyroid hormone including teriparatide; and anticholinergics such as scopolamine. Examples of agents that have profound physiological effects at low doses include, without limitation, antihypertensives and/or blood pressure down regulators. Examples of analgesics include, without limitation, fentanyl, fentanyl citrate, morphine, meperidine, and other opioids. Examples of immunomodulating agents include, without limitation, adalimumab (anti-tissue necrosis factor monoclonal antibody or anti-TNF). Examples of IL-1 receptor antagonists include, without limitation, anakinra. Examples of IL-2 alpha receptor antagonists include, without limitation, daclizumab and basiliximab. Examples of anti-rejection compounds include, without limitation, azathioprine, cyclosporine, and tacrolimus. Examples of hormonal agents include, without limitation, testosterone, estrogen, growth hormone, insulin, thyroid hormone, follicle stimulating hormone (FSH), epinephrine/adrenaline, progesterone, parathyroid hormone, gonadotrophin releasing hormone (GHRH), leutinizing hormone releasing hormone (LHRH), other hormones such as those where contact with the hormone by members of the opposite sex can lead to side effects, and derivatives thereof. Examples of prostaglandins include, without limitation, gamma-linolenic acid, docosahexanoic acid, arachidonic acid and eicosapentaenoic acid. Examples of sedatives include, without limitation, barbiturates such as amobarbital, pentobarbital, secobarbital, and phenobarbitol; benzodiazepines such as clonazepam, diazepam, estazolam, flunitrazepam, lorazepam, midazolam, nitrazepam, oxazepam, triazolam, temazepam, chlordiazepoxide, and alprazolam; herbal sedatives such as ashwagandha, duboisia hopwoodii, prosanthera striatiflora, kava (piper methysticum), mandrake, valerian, and marijuana; non-benzodiazepine sedatives (a.k.a. "Z-drugs") such as eszopiclone, zaleplon, zolpidem, zopiclone; antihistamines such as diphenhydramine, dimenhydrinate, doxylamine, and promethazine; and other sedatives such as chloral hydrate. Examples of anticholinergic agents include, without limitation, dicyclomine, atropine, ipratropium bromide, oxitropium bromide, and tiotropium. Examples of Parkinson's disease drugs include, without limitation, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, and lisuride. Examples of expensive agents include, without limitation, human growth hormone and erythropoietin. Examples of neuroleptic agents includes, without limitation, antipsychotics; butyrophenones such as haloperidol and droperidol; phenothiazines such as chlorpromazine, fluphenazine, perphenazine, prochlorperazine, thioridazine, trifluoperazine, mesoridazine, periciazine, promazine, triflupromazine, levomepromazine, promethazine, and pimozide; thioxanthenes such as chlorprothixene, clopenthixol, flupenthixol, thiothixene, and zuclopenthixol; atypical antipsychotics such as clozapine, olanzapine, risperidone, quetiapine, ziprasidone, amisulpride, asenapine, paliperidone, iloperidone, zotepine, and sertindole; and third generation antipsychotics such as aripiprazole and bifeprunox. Examples of TNF blockers includes, without limitation, etanercept.

In some embodiments, the hazardous agent can be selected from botulinum toxin, injectable gold, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, dexamethasone, progesterone, somatostatin, analogues of dexamethasone, analogues of progesterone, analogues of somatostatin, teriparatide, scopolamine, antihypertensives, blood pressure down regulators, fentanyl, fentanyl citrate, morphine, meperidine, other opioids, adalimumab (anti-tissue necrosis factor monoclonal antibody or anti-TNF), anakinra, daclizumab, basiliximab, azathioprine, cyclosporine, tacrolimus, testosterone, estrogen, growth hormone, insulin, thyroid hormone, follicle stimulating hormone (FSH), epinephrine/adrenaline, gamma-linolenic acid, docosahexanoic acid, arachidonic acid, eicosapentaenoic acid, amobarbital, pentobarbital, secobarbital, phenobarbitol, clonazepam, diazepam, estazolam, flunitrazepam, lorazepam, midazolam, nitrazepam, oxazepam, triazolam, temazepam, chlordiazepoxide, alprazolam, ashwagandha, duboisia hopwoodii, prosanthera striatiflora, kava (piper methysticum), mandrake, valerian, marijuana, eszopiclone, zaleplon, zolpidem, zopiclone, diphenhydramine, dimenhydrinate, doxylamine, promethazine, chloral hydrate, dicyclomine, atropine, ipratropium bromide, oxitropium bromide, tiotropium, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, lisuride, human growth hormone, erythropoietin, haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, etanercept, derivatives of any of the foregoing, and combinations of any of the foregoing.

C. Methods of Use

The initiation of treatment with a hazardous agent can be an important stage in the management of a disease condition in a patient. The amount of hazardous agent administered may require adjustment based on the patient response. Adverse events and clinical endpoints may result in the requirement for dose alteration. As many patients are unable to achieve certain clinical endpoints on an oral therapy alone and given the progressive nature of many diseases, it can be advantageous to switch these patients, who are on an oral therapies, to parenteral equivalents of the oral therapies in order for the patients to achieve desired clinical endpoints. In practice, however, there are far fewer parenteral equivalents of oral therapies than there are oral therapies.

Accordingly, for many physicians and patients the option of switching patients from ineffective oral therapies to more effective parenteral equivalents is simply nonexistent.

Accordingly, in one aspect, the present invention provides a method for treatment that includes treating a patient with an injectable subcutaneous dose of a hazardous agent based on a known oral dose of the hazardous agent. In one embodiment, the method for treatment includes (a) selecting a dose level of a hazardous agent for subcutaneous administration to a patient, wherein the selected dose level of the hazardous agent for subcutaneous administration is equivalent to the known oral dose of the hazardous agent. In one embodiment, the method for treatment includes subcutaneously administering the hazardous agent to the patient at the selected dose level. In one embodiment, the method for treatment includes evaluating the patient's response to the subcutaneously administered dose level of the hazardous agent. In one embodiment, the method for treatment includes changing or maintaining the selected dose level of the hazardous agent on the basis of the patient's response to the subcutaneously administered dose of the hazardous agent.

An exemplary method for determining an injectable subcutaneous dose of the hazardous agent based on a known oral dose of a particular hazardous agent is disclosed in U.S. Patent Application No. 61/713,197 entitled "Method Of Determining An Injected Dose Based On A Known Oral Dose" (to Peter L. Sadowski et al.), which is incorporated herein by reference in its entirety. In one embodiment, the oral dose of methotrexate to be converted to an equivalent subcutaneous dose of methotrexate ranges from about 7.5 mg to about 30 mg.

In one embodiment, the step of evaluating the patient's response to the subcutaneously administered dose level of the hazardous agent includes monitoring or measuring one or more clinical endpoints in the patient. In one embodiment, any suitable potential clinical endpoint can be used to evaluate the patient's response to the subcutaneously administered dose level of the hazardous agent. In one embodiment, the clinical endpoint is one that might reasonably be predicted to occur as a result of the subcutaneously administered dose level of the hazardous agent. In one embodiment, the endpoint can be ordinal in nature, i.e. it is possible to rank order the outcomes from worst to best. In one embodiment, the endpoint can be quantifiable in nature (for example, amenable to a direct numeric measurement), but this is not a necessary condition for the practice of the present invention.

Suitable clinical endpoints include, but are not limited, to blood pressure, blood chemistries, fasting plasma glucose, forced expiratory volume, swollen joints, the reported number of side effects a patient is experiencing each week, a survival time, patient's overall survival time (OS), the disease free survival time (DFS), the probability that a treatment, therapy or drug will be successful or effective, the probability of getting a specific disease, the disease recurrence probability, the patient's disposition to having a heart attack or stroke, or the patient's life expectancy. Those of skill in the art will recognize that many suitable endpoints exist which may be measured in the practice of the present invention, and all such endpoints are intended to be encompassed in the scope of the instant invention.

Once the desired clinical endpoint is achieved, treatment with the hazardous agent does not necessarily cease. In one embodiment, administration of the selected dose level of the hazardous agent for subcutaneous administration to a patient is continued as a maintenance dose. In one embodiment, the method of treatment includes multiple clinical endpoints. In one such embodiment, the method of treatment includes changing dose level of the hazardous agent based on the patient's response to the subcutaneously administered dose level of the hazardous agent. In one embodiment, changing dose level of the hazardous agent comprises decreasing a current subcutaneous dose of the hazardous agent being used in the treatment of the patient to a lower subcutaneous dose level of the hazardous agent. In one embodiment, changing dose level of the hazardous agent comprises increasing a current subcutaneous dose of the hazardous agent being used in the treatment of the patient to a higher subcutaneous dose level of the hazardous agent.

In some exemplary embodiments, the method of treatment includes hazardous agent dose titration, wherein the hazardous agent dose titration includes performing the steps of: (i) evaluating the patient's response to the subcutaneously administered dose level of the hazardous agent, and (ii) changing the selected dose level of the hazardous agent based on the patient's response to subcutaneously administered dose level of the hazardous agent multiple times during the course of treatment. In one embodiment of the hazardous agent dose titration, evaluating the patient's response to the subcutaneously administered dose level of the hazardous agent includes using one or more measurements for one or more clinical endpoints to determine appropriate dose levels of the hazardous agent which can produce improved clinical responses in patients while simultaneously minimizing the adverse side effects the patients may experience. In one embodiment, the hazardous agent dose titration is used to minimize adverse side effects which include, but are not limited to, weakness of the face, arm and/or leg on one side of the body, numbness in the face, arm, and/or leg on one side of the body, inability to understand spoken language, inability to speak or speak clearly, inability to write, vertigo and/or gait imbalance, double vision and an unusually severe headache.

In one embodiment of the hazardous agent dose titration, the dosage of the hazardous agent or the frequency of subcutaneous administration of the hazardous agent, or both, may be reduced, on the basis of the patient's response to a level at which a target clinical endpoint is maintained or improved patient's condition is retained. In one embodiment, the hazardous agent dose titration enables compliance with a regimen of changing dosage of the hazardous agent over a period of time. In one embodiment of the hazardous agent dose titration, the step of evaluating the patient's response includes consideration of the patient's age, weight, and/or other factors specific to the patient. In one embodiment, the hazardous agent dose titration is continued until a favorable balance between a desired response in the patient and undesirable side effects is achieved. In one embodiment, the hazardous agent dose titration method employs a constant volume of the pharmaceutical composition across all dosages of the hazardous agent administered during the course of a treatment. Maintaining a constant volume of the pharmaceutical composition across all dosages of the hazardous agent helps comfort the patient because of habituation to the same injection volume, which in turn improves patient medication adherence, making dose escalation easier and more precise.

The method of treatment in accordance with the present invention, including the titration technique therein, can be used in treating any of a number of diseases and/or conditions. In one embodiment, the method of treatment is used in treating a disease condition that includes, without limitation, cancer, AIDS, arthritis, diabetes, and hypertension. In one embodiment, the method of treatment is used in treating an autoimmune condition. In one embodiment, the method of treatment is used in treating an autoimmune condition, wherein the autoimmune condition is selected from the group consisting of multiple sclerosis, Type I diabetes mellitus, rheumatoid arthritis, lupus erythematosus, psoriasis, Myasthenia Gravis, Graves' disease, Hashimoto's thyroiditis, Sjogren's syndrome, ankylosing spondylitis, and inflammatory bowel disease. In one embodiment, the method of treatment is used in treating rheumatoid arthritis, juvenile rheumatoid arthritis, psoriasis, psoriatic arthritis, systemic lupus erythematosus, steroid-resistant polymyositis or dermatomyositis, Wegener's granulomatosis, polyarteritis nodosa, and some forms of vasculitis.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

All references, including publications, patent applications, and patents, cited herein are hereby incorporated by reference to the same extent as if each reference were individually and specifically indicated to be incorporated by reference and were set forth in its entirety herein.

We claim:

1. A medical kit comprising:
a first kit comprising at least two prefilled syringes configured to deliver methotrexate subcutaneously to a patient in need thereof and instructions for the use of the syringes,
wherein the prefilled syringes of the first kit include a pharmaceutical composition comprising a dose of methotrexate in a volume of a pharmaceutically acceptable solvent that includes water or ethanol,
wherein the dose of methotrexate is in a range of from about 7.5 mg to about 25 mg,
wherein the volume of the pharmaceutical composition in the prefilled syringes of the first kit is greater than 0.01 ml but less than or equal to 1 ml and the concentration of the methotrexate in the prefilled syringes is 25 mg/ml, and
wherein the first kit does not include an autoinjector, and
a second kit comprising at least two prefilled syringes configured to deliver methotrexate subcutaneously to a patient in need thereof and instructions for the use of the syringes,
wherein the prefilled syringes of the second kit include a pharmaceutical composition comprising a dose of methotrexate in a volume of a pharmaceutically acceptable solvent that includes water or ethanol,
wherein the dose of methotrexate is in a range of from about 7.5 mg to about 25 mg,
wherein the volume of the pharmaceutical composition in the prefilled syringes of the second kit is greater than 0.01 ml but less than or equal to 1ml and the concentration of the methotrexate in the prefilled syringes is 25 mg/ml,
wherein the second kit does not include an autoinjector, and
wherein the volume of the prefilled syringes of the second kit is different than the volume of the prefilled syringes of the first kit.

2. A method to provide methotrexate comprising:
providing a first kit comprising at least two prefilled syringes configured to deliver methotrexate subcutaneously to a patient in need thereof and instructions for the use of the syringes,
wherein the prefilled syringes of the first kit include a pharmaceutical composition comprising a dose of methotrexate in a volume of a pharmaceutically acceptable solvent that includes water or ethanol,
wherein the dose of methotrexate is in a range of from about 7.5 mg to about 25 mg
wherein the volume of the pharmaceutical composition in the prefilled syringes of the first kit is greater than 0.01 ml but less than or equal to 1 ml and the concentration of the methotrexate in the prefilled syringes is 25 mg/ml; and
wherein the first kit does not include an autoinjector and
providing a second kit comprising at least two prefilled syringes configured to deliver methotrexate subcutaneously to a patient in need thereof and instructions for the use of the syringes,
wherein the prefilled syringes of the second kit include a pharmaceutical composition comprising a dose of methotrexate in a volume of a pharmaceutically acceptable solvent that includes water or ethanol,
wherein the dose of methotrexate is in a range of from about 7.5 mg to about 25 mg,
wherein the volume of the pharmaceutical composition in the prefilled syringes of the second kit is greater than 0.01 ml but less than or equal to 1 ml and the concentration of the methotrexate in the prefilled syringes is 25 mg/ml, wherein the second kit does not include an autoinjector, and wherein the volume of the prefilled syringes of the second kit is different than the volume of the prefilled syringes of the first kit.

3. The method of claim 2, further comprising:
providing a third kit comprising at least two prefilled syringes configured to deliver methotrexate subcutaneously to a patient in need thereof and instructions for the use of the syringes,
wherein the prefilled syringes of the third kit include a pharmaceutical composition comprising a dose of methotrexate in a volume of a pharmaceutically acceptable solvent that includes water or ethanol,
wherein the dose of methotrexate is in a range of from about 7.5 mg to about 25 mg
wherein the volume of the pharmaceutical composition in the prefilled syringes of the third kit is greater than 0.01 ml but less than or equal to 1 ml and the concentration of the methotrexate in the prefilled syringes is 25 mg/ml,
wherein the third kit does not include an autoinjector, and
wherein the volume of the prefilled syringes of the third kit is different than the volume of the prefilled syringes of the first and second kits.

4. The method of claim 3, further comprising:
providing a fourth kit comprising at least two prefilled syringes configured to deliver methotrexate subcutaneously to a patient in need thereof and instructions for the use of the syringes,
wherein the prefilled syringes of the fourth kit include a pharmaceutical composition comprising a dose of methotrexate in a volume of a pharmaceutically acceptable solvent that includes water or ethanol,
wherein the dose of methotrexate is in a range of from about 7.5mg to about 25 mg,
wherein the volume of the pharmaceutical composition in the prefilled syringes of the fourth kit is greater than 0.001ml but less than or equal to 1 ml and the concentration of the methotrexate in the prefilled syringes is 25 mg/ml,
wherein the fourth kit does not include an autoinjector, and
wherein the volume of the prefilled syringes of the fourth kit is different than the volume of the prefilled syringes of the first, second and third kits.

5. The method of claim 4, further comprising:
providing a fifth kit comprising at least two prefilled syringes configured to deliver methotrexate subcutaneously to a patient in need thereof and instructions for the use of the syringes,
wherein the prefilled syringes of the fifth kit include a pharmaceutical composition comprising a dose of methotrexate in a volume of a pharmaceutically acceptable solvent that includes water or ethanol,
wherein the dose of methotrexate is in a range of from about 7.5 mg to about 25 mg,
wherein the volume of the pharmaceutical composition in the prefilled syringes of the fifth kit is greater than 0.01 ml but less than or equal to 1 ml and the concentration of the methotrexate in the prefilled syringes is 25 mg/ml,
wherein the fifth kit does not include an autoinjector, and
wherein the volume of the prefilled syringes of the fifth kit is different than the volume of the prefilled syringes of the first, second, third and fourth kits.

6. The method according to claim 2, wherein the dose of methotrexate in the prefilled syringes of the first kit is selected from the group consisting of 7.5mg, 10mg, 12.5 mg, 15 mg, 17.5 mg, 20 mg, 22.5 mg, and 25 mg.

7. The method according to claim 3, wherein the dose of methotrexate in the prefilled syringes of the third kit is selected from the group consisting of 7.5 mg, 10 mg, 12.5 mg, 15 mg, 17.5 mg, 20 mg, 22.5 mg, and 25 mg.

8. The method according to claim 4 wherein the dose of methotrexate in the prefilled syringes of the fourth kit is selected from the group consisting of 7.5 mg, 10 mg, 12.5 mg, 15mg, 17.5 mg, 20 mg, 22.5 mg, and 25 mg.

9. The method according to claim 5, wherein the dose of methotrexate in the prefilled syringes of the fifth kit is selected from the group consisting of 7.5 mg, 10 mg, 12.5 mg, 15 mg, 17.5 mg, 20 mg, 22.5 mg, and 25 mg.

10. The method according to claim 2, wherein the volume of the prefilled syringes of the first kit is selected from 0.3 ml, 0.4 ml, 0.6 ml, 0.8 ml and 1.0 ml.

11. The method according to claim 3, wherein the volume of the prefilled syringes of the third kit is selected from 0.3 ml, 0.4 ml, 0.6 ml, 0.8 ml and 1.0 ml.

12. The method according to claim 4, wherein the volume of the prefilled syringes of the fourth kit is selected from 0.3 ml, 0.4 ml, 0.6 ml, 0.8 ml and 1.0 ml.

13. The method according to claim 5, wherein the volume of the prefilled syringes of the fifth kit is selected from 0.3 ml, 0.4 ml, 0.6 ml, 0.8 ml and 1.0 ml.

14. The method according to claim 13, wherein the volume of the prefilled syringes of the first kit is selected from 0.3 ml, 0.4 ml, 0.6 ml, 0.8 ml and 1.0 ml.

15. The method according to claim 14, wherein the volume of the prefilled syringes of the second kit is selected from 0.3 ml, 0.4 ml, 0.6 ml, 0.8 ml and 1.0 ml.

16. The method according to claim 15, wherein the volume of the prefilled syringes of the third kit is selected from 0.3 ml, 0.4 ml, 0.6 ml, 0.8 ml and 1.0 ml.

17. The method according to claim 16, wherein the volume of the prefilled syringes of the fourth kit is selected from 0.3 ml, 0.4 ml, 0.6 ml, 0.8 ml and 1.0 ml.

* * * * *